United States Patent
Kawakami et al.

(10) Patent No.: US 6,582,434 B2
(45) Date of Patent: Jun. 24, 2003

(54) VERTEBRAL CONNECTING ROD AND SPINAL OSTEOSYNTHESIS DEVICE USING THE SAME

(75) Inventors: Noriaki Kawakami, Aichi (JP); Koji Sato, Aichi (JP); Yukihiro Matsuyama, Aichi (JP); Kazuya Oribe, Tokyo (JP); Hiroshi Takamido, Nagoya (JP)

(73) Assignee: Showa Ika Kohgyo Co., Ltd., Aichi-Ken (JP)

( * ) Notice: Subject to any disclaimer, the term of this patent is extended or adjusted under 35 U.S.C. 154(b) by 0 days.

(21) Appl. No.: 09/880,072

(22) Filed: Jun. 14, 2001

(65) Prior Publication Data

US 2002/0193793 A1 Dec. 19, 2002

(51) Int. Cl.[7] ............................................... A61B 17/56
(52) U.S. Cl. ....................................................... 606/61
(58) Field of Search ............................. 606/60, 61, 59, 606/72

(56) References Cited

U.S. PATENT DOCUMENTS

| | | | |
|---|---|---|---|
| 5,181,917 A | * | 1/1993 | Rogozinski .................. 606/61 |
| 5,387,213 A | * | 2/1995 | Breard et al. ................. 606/61 |
| 5,562,737 A | | 10/1996 | Graf |
| 5,704,936 A | * | 1/1998 | Mazel .......................... 606/61 |
| 5,725,582 A | | 3/1998 | Bevan et al. |
| 5,910,142 A | * | 6/1999 | Tatar ............................ 606/61 |
| 5,989,251 A | | 11/1999 | Nichols |
| 6,063,089 A | * | 5/2000 | Errico et al. ................. 606/61 |
| 6,077,263 A | * | 6/2000 | Ameil et al. ................. 606/61 |

FOREIGN PATENT DOCUMENTS

| | | |
|---|---|---|
| FR | 2726459 | 5/1996 |
| WO | 96/14022 | 5/1996 |

* cited by examiner

*Primary Examiner*—Eduardo C. Robert
(74) *Attorney, Agent, or Firm*—Greenblum & Bernstein, P.L.C.

(57) ABSTRACT

A vertebral connecting rod and a spinal osteosynthesis device are disclosed. The vertebral connecting rod 1, which is adapted to be rigidly supported with a pair of spinal implants 5, 5 anchored to vertebral bodies 3, 3 such as thoracic vertebrae or lumbar vertebrae etc., has a pin-shaped section 7 of which one distal end formed with a hook segment 11 for hanging an interconnecting member 9. A slip-out protective member 19 is engageable with the hook segment 11. In a preferred embodiment, the pin-shaped section has at its arbitrary position formed with an engagement convex segment 27 adapted to engage with a corresponding engagement concave recess formed in the spinal implant 5.

11 Claims, 5 Drawing Sheets

VERTEBRAL CONNECTING ROD AND SPINAL OSTEOSYNTHESIS DEVICE USING THE SAME

BACKGROUND OF THE INVENTION

The present invention relates to spinal osteosynthesis devices for interconnecting vertebral bodies such as thoracic vertebrae or lumbar vertebrae, etc., and, more particularly, to a vertebral connecting rod and a spinal osteosynthesis device using the same.

In recent years, it has been a usual practice to employ a spinal osteosynthesis device which includes spinal implants, each of which has a U-shaped engagement recess, anchored to separated vertebral bodies such as thoracic vertebrae, lumbar vertebrae etc., and a vertebral connecting rod which has distal ends rigidly supported by screwing fixture plugs into the respective spinal implants.

Further, it has been proposed to anchor the spinal implants to the separated vertebral bodies, with one of the implant having a head portion formed with an L-shaped hooking segment for hanging an interconnecting member such as an artificial ligament, a wire or a cable, etc., for thereby interconnecting the vertebral bodies such as the lumbar vertebrae.

Consequently, in the event that one osseous interconnecting structure employing the vertebral rod and another osseous interconnecting structure employing the interconnecting member are located in a series, it has been a usual practice to anchor one of the spinal implants, which rigidly supports the distal ends of the vertebral connecting rod, and another spinal implant, which hangs the interconnecting member, into a common vertebral body in close proximity relationship.

As a result, the spinal implant, which rigidly supports the vertebral connecting rod, and the spinal implant, which hangs the interconnecting member, are subjected to mutually interfering with one another while disturbing the operation of a manipulation tool for screwing a fixture plug into the spinal implant. Another severe issue is encountered in the above practice in that the presence of the two spinal implants anchored to the common vertebral body exerts a significantly large load thereto.

SUMMARY OF THE INVENTION

The present invention has been made with a view to overcoming the various disadvantages encountered in prior art devices and it is therefore an object of the present invention to provide a vertebral connecting rod and a spinal osteosynthesis device using the same.

According to a first aspect of the present invention, there is provided a vertebral connecting rod for interconnecting vertebral bodies, which comprises a pin-shaped section rigidly supported by one of spinal implants anchored to the vertebral bodies, and a hooking segment formed on at least one of distal ends of the pin-shaped section, wherein the hook segment serves to hang an interconnecting member hanged to another one of the spinal implants anchored to the vertebral bodies.

According to a second aspect of the present invention, there is provided a vertebral connecting rod which further comprises a slip-out protective member engageable with the hook segment for preventing the interconnecting member, which is hanged with the hooking segment, from slipping out from the hook segment.

According to a third aspect of the present invention, there is provided a vertebral connecting member, wherein the pin-shaped section has at its arbitrary position formed with an engagement convex segment engageable with an engagement concave recess formed in the one of the spinal implants.

According to a fourth aspect of the present invention, there is provided a vertebral connecting rod, wherein the hook segment has a U-shaped hanging recess.

According to a fifth aspect of the present invention, there is provided a vertebral connecting rod, wherein the U-shaped hanging recess has an entrance portion formed with a pair of engaging protrusions.

According to a six aspect of the present invention, there is provided a vertebral connecting rod, wherein the pair of engaging protrusions have distal ends formed with outwardly extending minute projections, respectively.

According to a seventh aspect of the present invention, there is provided a vertebral connecting rod, wherein the slip-out protective member comprises a slid cap having slide recesses engageable with the minute protections, respectively.

According to an eighth aspect of the present invention, there is provided a vertebral connecting rod, wherein the slip-out protective member is coupled to or uncoupled from the minute projections along longitudinal directions thereof.

According to a ninth aspect of the present invention, there is provided a vertebral connecting rod, wherein the slip-out protective member is coupled to or uncoupled from the minute projections in a direction perpendicular to a longitudinal axis of the pin-shaped section.

According to a tenth aspect of the present invention, there is provided a vertebral connecting rod, wherein the hook segment has a substantially L-shaped configuration.

According to an eleventh aspect of the present invention, there is provided a vertebral connecting rod, wherein the L-shaped configuration has a distal end formed with an engaging protrusion.

According to a twelfth aspect of the present invention, there is provided a vertebral connecting rod, wherein the hook segment has a substantially U-shaped configuration.

According to a thirteenth aspect of the present invention, there is provided a vertebral connecting rod, wherein the U-shaped configuration has an entrance portion formed with a protrusion extending in a direction to close the entrance portion.

According to a fourteenth aspect of the present invention, there is provided a spinal osteosynthesis device for interconnecting vertebral bodies, which comprises a pair of spinal implants adapted to be anchored to the vertebral bodies to be interconnected, a hooking spinal implant adapted to be anchored to the vertebral body, a vertebral connecting rod rigidly supported by the pair of spinal implants and having its one end formed with a hook segment, and an interconnecting member adapted to be hanged between the spinal implant and the hook segment of the vertebral connecting rod.

Thus, in on aspect, the present invention is directed to a vertebral connecting rod for interconnecting vertebral bodies, comprising an elongated section including distal ends, the elongated section being capable of being rigidly supported by a spinal implant; a hook segment formed on at least one of the distal ends of the elongated section, the hook segment serving to hang an interconnecting member capable of being connected to another spinal implant; and the elongated section including an engagement convex segment at an arbitrary position which engagement convex segment is capable of being engaged with a corresponding engagement concave recess formed in a spinal implant.

In another aspect, the present invention is directed to a vertebral connecting rod for interconnecting vertebral bodies, comprising an elongated section including distal ends, the elongated section being capable of being rigidly supported by a spinal implant; a hook segment formed on at least one of the distal ends of the elongated section, the hook segment including a U-shaped hanging recess serving to hang an interconnecting member capable of being connected to another spinal implant; and a slip-out protective member engageable with the hook segment for preventing the interconnecting member, when hung in the hook segment, from slipping out of the hook segment.

In still another aspect, the present invention is directed to a vertebral connecting rod for interconnecting vertebral bodies, comprising an elongated section including distal ends, the elongated section being capable of being rigidly supported by a spinal implant; a hook segment formed on at least one of the distal ends of the elongated section, the hook segment including an L-shaped configuration serving to hang an interconnecting member capable of being connected to another spinal implant; and the L-shaped configuration comprising a distal end formed with an engaging protrusion.

In still another aspect, the present invention is directed to a spinal osteosynthesis device for interconnecting vertebral bodies, comprising a pair of spinal implants adapted to be anchored to vertebral bodies to be interconnected; a hooking spinal implant adapted to be anchored to the vertebral body; a vertebral connecting rod rigidly supported by the pair of spinal implants and having one end formed with a hook segment which includes a U-shaped hanging recess; and an interconnecting member adapted to be hanged between the hooking spinal implant and the hook segment of the vertebral connecting rod.

Other aspect and advantages of the invention will become more apparent from the following description, taken in conjunction with the accompanying drawings, illustrating by way of example the principles of the invention.

DETAILED DESCRIPTION OF THE PREFERRED EMBODIMENTS

Figure 1:
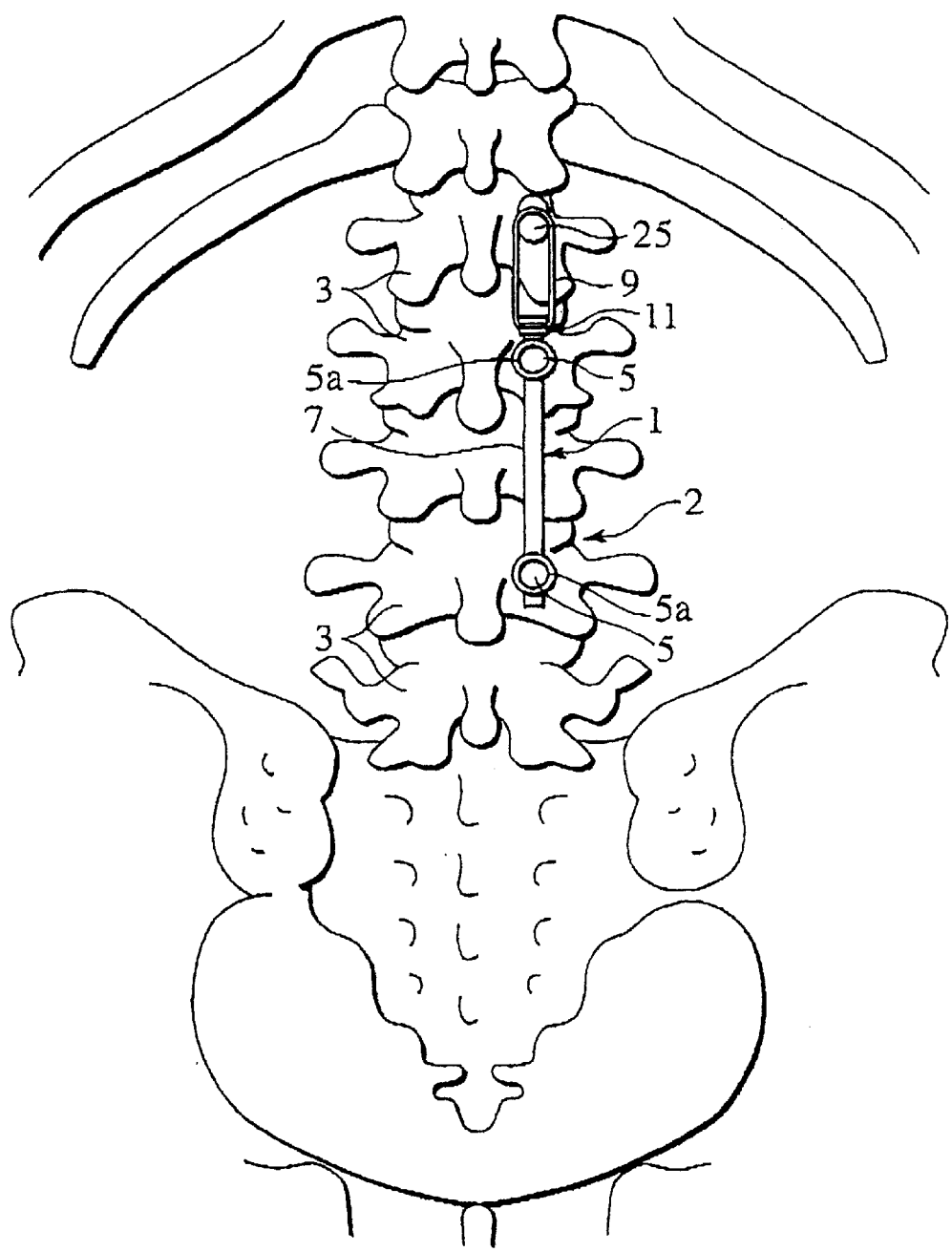
FIG. 1 is a schematic view of a vertebral connecting rod of a first preferred embodiment according to the present invention as applied to a spinal osteosynthesis device for interconnecting vertebral bodies.

Referring to the drawings and more particularly to FIG. 1, there is shown a vertebral connecting rod 1 of a first preferred embodiment according to the present invention for use in a spinal osteosynthesis device 2 for interconnecting plural vertebral bodies 3, 3, which are spaced from one another, such as thoracic vertebrae, lumbar vertebrae, etc., in a fixed place.

The spinal osteosynthesis device 2 includes a pair of spinal implants 5, 5 which are anchored to the vertebral bodies 3, 3, respectively, which are spaced from one another. Distal ends of the vertebral connecting rod 1 are fixedly supported with head portions of respective spinal implants 5, 5 in a unitary structure. Each of the spinal implants 5, 5 includes a screw segment which is screwed into and anchored in the vertebral body 3, and the head portion 5a formed at an upper end of the screw segment and having a U-shaped rod engagement recess or rod engagement bores, with the head portion 5a having a threaded end into which a fixture plug is screwed to firmly retain the distal end of the vertebral connecting 1 in the head portion 5a of the spinal implant 5. The spinal implant 5 of such a configuration may include a known structure and, therefore, a detailed description of the same is herein omitted for the sake of simplicity.

As seen in FIG. 1, the vertebral connecting rod 1 includes an elongated pin-shaped section 7 extending between the adjacent spinal implants 5, 5 and fixedly supported thereby. The pin-shaped section 7 has a length that is arbitrarily determined so as to meet a distance between the adjacent vertebral bodies 3, 3 to be interconnected. A distal end of the pin-shaped section 7 has a hook segment 11 which hangs one end of an interconnecting member 9, such as an artificial ligament, a wire or a cable, etc., whose another end engages with a hooking spinal implant 25 anchored to another vertebral body 3.

Figure 2C:
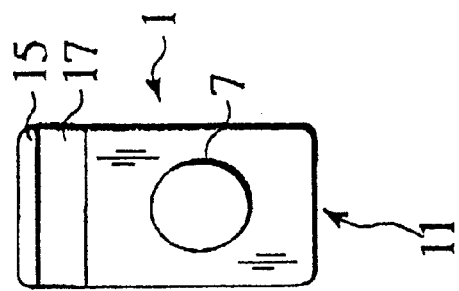
FIG. 2C is a side view of the hooking segment shown in FIG. 2A.
Figure 2B:
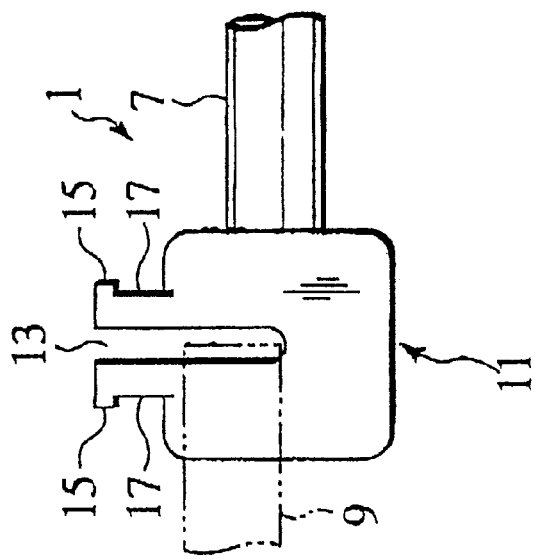
FIG. 2B is a front view of the hook segment shown in FIG. 2A.
Figure 2A:
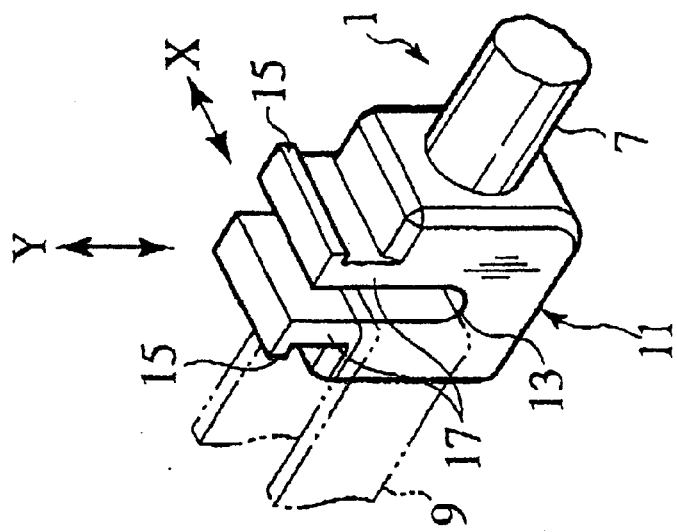
FIG. 2A is a perspective view of a hooking segment of the vertebral connecting rod shown in FIG. 1.
Figure 3A:
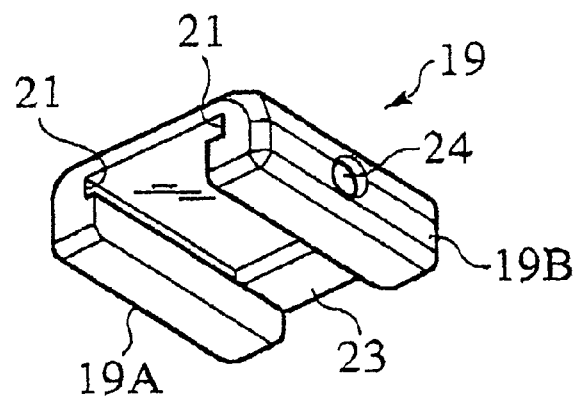
FIG. 3A is a perspective view of a slip-out protective member adapted to be coupled to or uncoupled from the hook segment shown in FIGS. 2A to 2C.
Figure 3B:
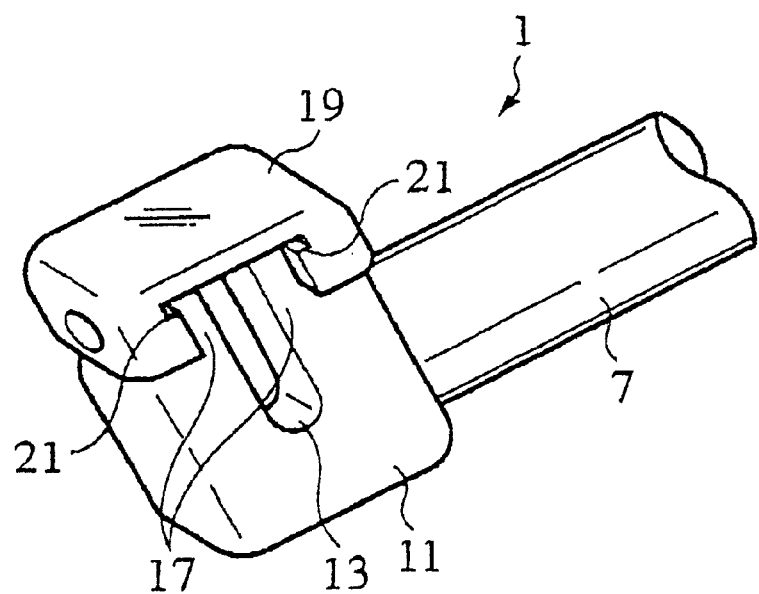
FIG. 3B is a perspective view of the vertebral connecting rod according to the present invention illustrating a condition wherein the slip-out protective member is held in coupled condition with the hook segment.

As clearly seen in FIGS. 2A to 2C, the hook segment 11 has a U-shaped hanging recess 13 which extends in substantially perpendicular to an axis of the pin-shaped section 7 for hanging the interconnecting member 9, with the hook segment 11 having a pair of lateral engagement protrusions 17, formed at an entrance of the hanging recess 13, which have minute projections or flanges 15 extending outward from distal ends of the lateral engagement protrusions 17, 17, respectively. As shown in FIGS. 3A and 3B, the vertebral connecting rod 1 also includes a slip-out protective member 19 which engages with the hook segment 11 to prevent the interconnecting member 9 from slipping out from the hanging recess 13 of the hook segment 11.

More particularly, the slip-out protective member 19 functions to prevent the interconnecting member 9 from disengaging from the entrance of the hanging recess 13. To this end, in the illustrated embodiment, the slip-out protective member 19 is formed in a profile of a slide cap which as a pair of laterally spaced slide recesses 21, 21 which are engageable with the minute projections 15 of the lateral engagement projections 17, 17, respectively. The slip-out protective member 19 also has a stopper 23 formed at rearmost ends of the respective slide recesses 21, 21 to be brought into abutting engagement with one side of each minute projections 15.

With such a structure discussed above, the slip-out protective member 19 is secured to the hook segment 11 by moving the slip-out protective member 19 in a direction as shown by an arrow X in FIG. 2A and coupling the slip-out protective member 19 to the pair of lateral engagement projections 17, 17 of the hook segment 11 to allow the minute projections 15, 15 to be held in sliding engagement with the slide recesses 21, 21 of the slip-out protective member 19 such that the entrance of the U-shaped hanging recess 13 of the hook segment 11 is closed with the slip-out protective member 19, as viewed in FIG. 3B, for thereby preventing the interconnecting member 9 from disengaging from the U-shaped hanging recess 13.

As previously noted, the distal ends of the pin-shaped section 7 of the vertebral connecting rod 1 are fixedly retained with the spinal implants 5, 5 anchored to the vertebral bodies 3, 3 for thereby interconnecting the vertebral bodies 3, 3 as a unitary structure. Then, the interconnecting member 19 is hanged between the hook segment 11, which is located outward from and closest to one of the spinal implants 5, 5, and the hooking spinal implant 25 which is anchored to the vertebral body 3 remaining adjacent to the vertebral body 3 in which one of the spinal implants 5, 5 is anchored as viewed in FIG. 1.

It will thus be seen that the vertebral connecting rod 1 has two functions, namely, a first function to interconnect the vertebral bodies 3, 3 spaced from one another and a second function to hang the interconnecting member 9. Consequently, even in a case where one osseous interconnecting structure employing the vertebral connecting rod 1 and another osseous interconnecting structure employing the interconnecting member 9 are consecutively located, it is unnecessary for the hooking spinal implant 25 to be located in close proximity to the spinal implant 5 which fixedly retains the vertebral connecting rod 1. Thus, the spinal implants can be mutually spaced from one another and do not interfere with one another, thereby avoiding plural spinal implants to be anchored in a single vertebral body to address the issues encountered in the prior art discussed above.

In the illustrated embodiment, although the slip-out protective member has been described as of the type wherein the slip-out protective member 19 is brought into engagement with or disengagement from the lateral engagement projections 17, 17 in the direction as shown by the arrows X in FIG. 2A, i.e., along their longitudinal directions, a modification may be made such that at least one of the lateral engagement projections 17, 17 and downward flanges 19A, 19B of the slip-out protective member 19 is resiliently formed to provide a deformable property to allow the slip-out protective member 19 from being coupled to or uncoupled from the lateral engagement projections 17, 17 of the hooking segment 11 in a direction as shown by an arrow Y in FIG. 2a, i.e., in a direction perpendicular to the longitudinal axis of the minute projections 15, 15. This results in an advantage wherein the slip-out protective member 19 is coupled to and uncoupled from the hook segment 11 within a limited narrow space.

During coupling or uncoupling operation of the slip-out protective member 19 relative to the lateral engagement projections 17, 17, it is highly probable to need an improved operability of the slip-out protective member 19 by manipulating the same with the use of a gripping tool (not shown). To this end, the downward flanges 19A, 19B of the slip-out protective member 19 have engagement apertures 24, 24, respectively, with which the gripping tool is engageable to be manipulated. By coupling the gripping tool to the engagement apertures 24, 24 of the slip-out protective member 19, the gripping tool may be manipulated to allow the slip-out protective member 19 to be coupled to or uncoupled from the lateral engagement projections 17, 17.

Figure 4:
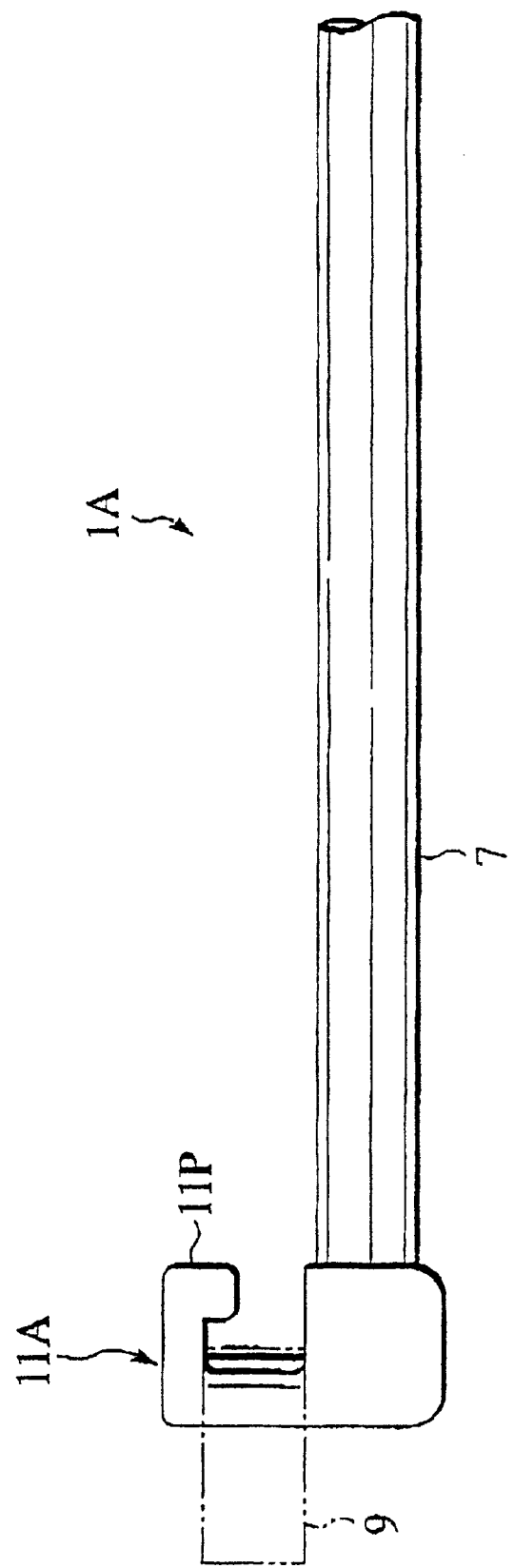
FIG. 4 is a view for illustrating a vertebral connecting rod of a second preferred embodiment according to the present invention.

FIG. 4 shows a second preferred embodiment of a vertebral connecting rod 1A according to the present invention. In the second preferred embodiment, the vertebral connecting rod 1A has at its distal end a hook segment 11A having a substantially L-shaped configuration. In such a structure of the vertebral connecting rod 1A, the presence of the L-shaped configuration of the hook segment 11A, formed at the distal end of the pin-shaped section 7, allows the hook segment 11A to have an engaging protrusion 11P which extends in a direction to close an entrance portion of the hook segment 11A to provide a slip-out protecting property to prevent the interconnecting member 9 from slipping out from the hook segment 11A in a more simplified fashion.

Figure 5:
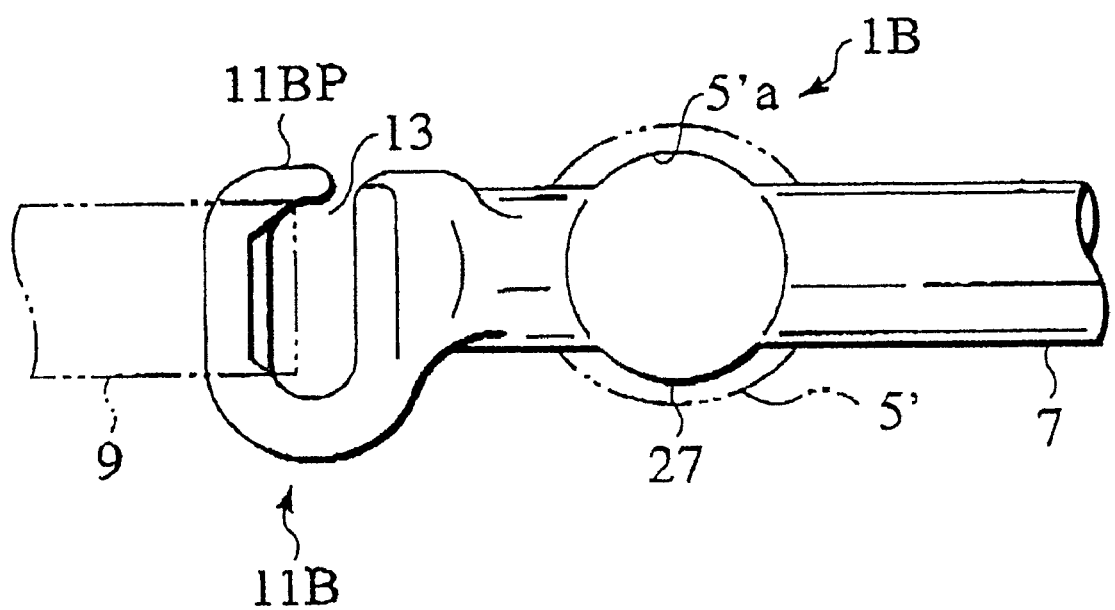
FIG. 5 is a view for illustrating a vertebral connecting rod of a third preferred embodiment according to the present invention.

FIG. 5 shows a third preferred embodiment of a vertebral connecting rod 1B according to the present invention. The distal end of the pin-shaped section 7 has a U-shaped hook segment 11B which has an entrance portion formed an engaging protrusion 11BP which extends in a direction to close the entrance portion to provide a slip-out protective property to prevent the interconnecting member 9 from slipping out from the hook segment 11B. Also, the rod 1B has a spherical-shaped, convex engagement segment 27 formed at a suitable position of the pin-shaped section 7 and adapted to be engageable with a spherical-shaped, concave engagement recess formed in the spinal implant (not shown).

With the rod 1B in such a structure discussed above, the convex engagement segment 27 of the rod 1B is brought into engagement with the corresponding concave engagement recess 5'a of the spinal implant 5', allowing the rod 1B to slightly swing in an arbitrary direction. Thus, it is possible for the hook segment 11B of the rod 1B to be directed toward a tensioned direction of the interconnecting member 9 in an increased amount of freedom while preventing the rod 1B from being dislocated from the spinal implant along the axis of the rod 1B. Accordingly, it is easy for the rod 1B to be directed in various directions to meet the tensioned angular direction of the interconnecting member 9 such that after the interconnecting member 9 has been hanged over the hook segment 11B of the rod 1B, the rod 1B can be readily fixed to the spinal implant by turning a stopper screw.

It will now be appreciated from the foregoing description that in accordance with the vertebral connecting rod and the spinal osteosynthesis device of the present invention, the presence of the hooking segment formed at the distal end of the pin-shaped section rigidly secured by the spinal implants anchored to the vertebral bodies allows the rod to have the first function to interconnect the separated vertebral bodies and the second function to hang the interconnecting member whereby even in a case where one osseous interconnecting structure employing the rod and another osseous interconnecting structure employing the interconnecting member are consecutively located, the vertebral connecting rod and the spinal osteosynthesis device of the present invention are enabled to meet various situations without causing an implantation of the plural spinal implants in a common vertebral body.

Further, the presence of the convex engagement segment formed on the pin-shaped section of the rod to be engageable with the corresponding concave engagement recess formed in the spinal implant allows the rod to slightly swing in a direction to meet the tensioned direction of the interconnecting member for thereby suitably adjusting the position of the rod relative to the tensioned state of the interconnecting member.

In addition, in the illustrated embodiments, although the rod of the present invention has been shown and described as applied to the vertebral connecting rod having its one distal end formed with the hook segment, both of the distal segments of the rod have the respective hook segments.

The present disclosure relates to subject matter contained in Japanese Patent Application No. 2000-137250, filed on May 10, 2000, the contents of which is herein expressly incorporated by reference in its entirety.

What is claimed is:

1. A vertebral connecting rod for interconnecting vertebral bodies, comprising:

an elongated section including distal ends, said elongated section being capable of being rigidly supported by a spinal implant;

a hook segment formed on at least one of said distal ends of the elongated section, said hook segment including a U-shaped hanging recess serving to hang an interconnecting member capable of being connected to another spinal implant; and a slip-out protective member engageable with said hook segment for preventing the interconnecting member, when hung in said hook segment, from slipping out of said hook segment.

2. A vertebral connecting rod according to claim 1, wherein said elongated section includes an engagement convex segment at an arbitrary position which engagement convex segment is capable of being engaged with a corresponding engagement concave recess formed in a spinal implant.

3. The vertebral connecting rod according to claim 1, wherein the hook segment has a substantially U-shaped configuration.

4. The vertebral connecting rod according to claim 3, wherein the U-shaped configuration has an entrance portion formed with a protrusion extending in a direction to close the entrance portion.

5. The vertebral connecting rod according to claim 1, wherein the U-shaped hanging recess has an entrance portion formed with a pair of engaging protrusions.

6. The vertebral connecting rod according to claim 5, wherein the pair of engaging protrusions have distal ends formed with outwardly extending minute projections, respectively.

7. The vertebral connecting rod according to claim 6, wherein the slip-out protective member comprises a slid cap having slide recesses engageable with the minute projections, respectively.

8. The vertebral connecting rod according to claim 7, wherein the slip-out protective member is coupled to or uncoupled from the minute projections along longitudinal directions thereof.

9. The vertebral connecting rod according to claim 7, wherein the slip-out protective member is coupled to or uncoupled from the minute projections in a direction perpendicular to a longitudinal axis of the pin-shaped section.

10. A vertebral connecting rod for interconnecting vertebral bodies, comprising:

an elongated section including distal ends, said elongated section being capable of being rigidly supported by a spinal implant;

a hook segment formed on at least one of said distal ends of the elongated section, said hook segment including an L-shaped configuration serving to hang an interconnecting member capable of being connected to another spinal implant; and said hook segment further comprising an engaging protrusion on said L-shaped configuration.

11. A spinal osteosynthesis device for interconnecting vertebral bodies, comprising:

a pair of spinal implants adapted to be anchored to vertebral bodies to be interconnected;

a hooking spinal implant adapted to be anchored to the vertebral body;

a vertebral connecting rod rigidly supported by the pair of spinal implants and having one end formed with a hook segment which includes a U-shaped hanging recess; and an interconnecting member adapted to be hanged between the hooking spinal implant and the hook segment of the vertebral connecting rod.

* * * * *